(12) United States Patent
Kusibojoska et al.

(10) Patent No.: US 6,764,479 B2
(45) Date of Patent: Jul. 20, 2004

(54) ABSORBENT ARTICLE

(75) Inventors: Liljana Kusibojoska, Malmögatan (SE); Kent Hermansson, Citrusgatan (SE); Kenneth Strannemalm, Brovägen (SE)

(73) Assignee: SCA Hygiene Products AB, Gothenburg (SE)

( * ) Notice: Subject to any disclaimer, the term of this patent is extended or adjusted under 35 U.S.C. 154(b) by 36 days.

(21) Appl. No.: 10/022,440

(22) Filed: Dec. 20, 2001

(65) Prior Publication Data

US 2002/0091370 A1 Jul. 11, 2002

Related U.S. Application Data

(60) Provisional application No. 60/256,481, filed on Dec. 20, 2000.

(30) Foreign Application Priority Data

Dec. 20, 2000 (SE) .............................................. 0004760

(51) Int. Cl.⁷ ................................................ A61F 13/15
(52) U.S. Cl. .................................... 604/385.3; 604/392
(58) Field of Search ........................... 604/385.24, 386, 604/389, 391, 392, 393, 394, 385.3

(56) References Cited

U.S. PATENT DOCUMENTS

| | | | | |
|---|---|---|---|---|
| 3,324,856 A | * | 6/1967 | Young .......................... | 604/394 |
| 4,381,781 A | | 5/1983 | Sciaraffa et al. | |
| 4,938,753 A | | 7/1990 | Van Gompel et al. | |
| 5,234,423 A | | 8/1993 | Alemany et al. | |
| 5,304,162 A | * | 4/1994 | Kuen .......................... | 604/391 |
| 5,370,634 A | * | 12/1994 | Ando et al. ............ | 604/385.21 |
| H1674 H | * | 8/1997 | Ames .......................... | 604/389 |
| 5,695,488 A | * | 12/1997 | Sosalla .................. | 604/385.24 |
| 5,997,521 A | | 12/1999 | Robles et al. | |
| 6,494,873 B2 | * | 12/2002 | Karlsson et al. ............ | 604/392 |
| 6,500,163 B2 | * | 12/2002 | Ronnberg et al. ........... | 604/392 |
| 2002/0010455 A1 | * | 1/2002 | Hermansson et al. .. | 604/385.24 |
| 2002/0032425 A1 | * | 3/2002 | Hjorth .................... | 604/385.01 |
| 2002/0032426 A1 | * | 3/2002 | Lindstrom et al. ...... | 604/385.01 |

FOREIGN PATENT DOCUMENTS

| | | |
|---|---|---|
| EP | 0 287 388 A2 | 10/1988 |
| EP | 0 287 388 A3 | 10/1988 |
| EP | 0 528 282 A2 | 2/1993 |
| EP | 0 528 282 A3 | 2/1993 |
| EP | 0 409 307 B1 | 9/1996 |
| EP | 0 605 012 B1 | 3/1999 |
| FR | 2 586 558 | 3/1987 |
| GB | 2 292 067 B | 2/1996 |
| SE | 504 624 | 3/1997 |

* cited by examiner

Primary Examiner—John J. Calvert
Assistant Examiner—C. Lynne Anderson
(74) Attorney, Agent, or Firm—Young & Thompson

(57) ABSTRACT

Absorbent article such as a diaper and an incontinence guard includes a pair of belt portions attached to the rear portion or alternatively to the front portion of the article. The belt portions are fastened together around the waist of the wearer, wherein the one belt portion carries a first fastener arrangement intended to be attached against the opposite belt portion. The front portion or alternatively the rear portion exhibits a second fastener arrangement intended to be attached to the belt portions in such a way that the article will assume a pantlike shape, where the belt portions form a part of the waist portions of the pant. The belt portions are attached to the rear portion or alternatively to the front portion of the article via first elastic side panels arranged on the article. The front portion or alternatively the rear portion of the article has second elastic side panels to which the second fastener arrangement is attached.

6 Claims, 1 Drawing Sheet

ABSORBENT ARTICLE

Figure 1:
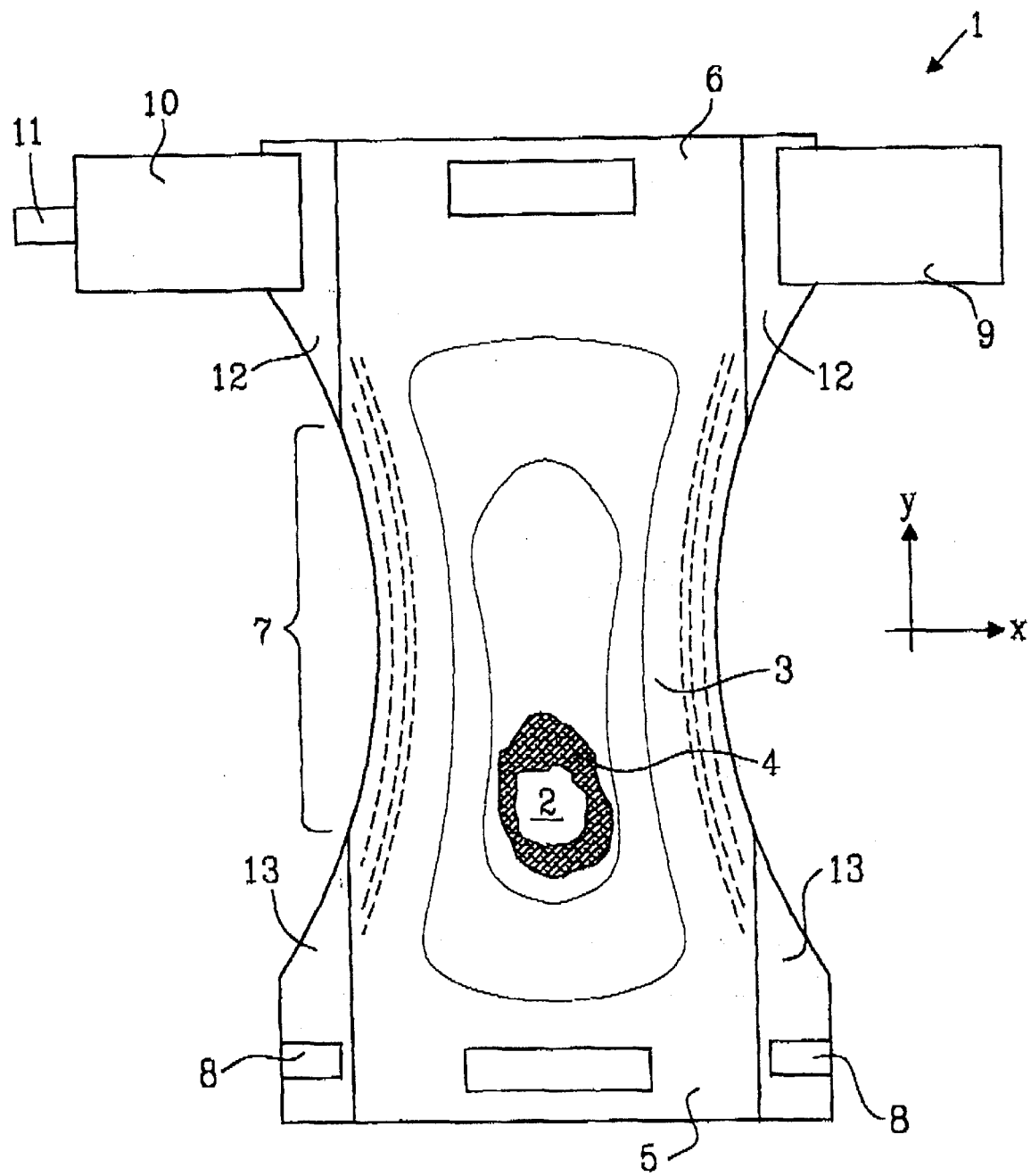

This application claims benefit of provisional application No. 60/256,481, filed Dec. 20, 2000.

TECHNICAL FIELD

The present invention relates to an absorbent article such as a diaper and an incontinence guard comprising a liquid permeable topsheet, a liquid impermeable backsheet and an absorbent body enclosed therebetween, wherein the article having a front portion, a rear portion and a crotch portion therebetween, and further is provided with a pair of belt portions attached to the rear portion, alternatively the front portion of the article and which are intended to be fastened together around the waist of the wearer by means of the first fastening means and where said front portion, alternatively the rear portion, is provided with attachment means intended to be attached to the belt portions, in such a way that the article will assume a pantlike shape, where the belt portions form a part of the waist portions of the pant.

BACKGROUND OF THE INVENTION

Diapers and incontinence guards usually exhibit a garment portion holding an absorbent body in place against the user's body and attachment means, which hold the garment portion in place also when the user is moving. A common type of attachment means are adhesive tapes or hook and loop fasteners of the touch-and-close type, which directly attach the front and rear portions of the absorbent article to each other. It is further known, through e.g., EP-A-0 287 388, EP-A-0 409 307, EP-A,0 528 282, EP-A0 605 012 and FRA-A-2 586 558, to attach the front and rear portions of the article by means of a belt, wherein the possibilities to adjust the fit are improved.

A conventional diaper for children is in general applied having the child in a lying position. The attachment means are usually arranged on the rear portion and are attached to the front portion. This kind of application often requires the aid from another person. However, for an adult user it is more desirable be able to self apply the incontinence guard. On a common type of belt diaper the belt portions are therefore first attached around the waist.

When the incontinence guard is fixed around the waist in this way, the user may reach after the rest of the incontinence guard between the legs and then the crotch portion of the incontinence guard is applied in the correct position by fastening the front portion of the diaper to the outside of the belt portions using hook and loop fasteners or tape tabs being arranged on the font portion and/or the belt portion. This design makes also possible for nursing personnel to apply the diaper on a standing person or for the user to apply the diaper on himself/herself in a standing position.

One problem is that the belt not properly adapts itself to the shape of the body it has been applied to, which leads to discomfort for the wearer at usage. The forces in the belt are concentrated to the centre potion of the belt and are generated from the fastening means on the belt, There are no forces acting in the upper or lower part of the belt. Often, the lower pat sits too firm and need to be able to loosen up whereas the upper part often needs to be closer to the body.

One way to solve this problem would be to use some kind of elastic material to make the product more flexible, However, the costs for the materials used in these products must be kept low, since these products are principally intended for one single use.

U.S. Pat. No. 5,695,488 describes a product mainly intended for children, which among others exhibit elastic waistbands arranged on the rear portion and which are intended to be attached around the waist portion of an user. However, these elastic waistbands are mainly there to assist on preventing leakage. On the other hand, to design the whole waist band using elastic materials is expensive. It is also difficult to combine a well working fastening system with elastic materials in the belt.

GB 2,292,067 shows a conventional diaper having elastic side portions on the rear portion on which fastening means are arranged. It only exhibits elastic materials in order to make sure that the fastening system itself will fit the wearer better, The document does not show a product being provided with a belt according to the present invention, which first is applied around the waist and then to attach the front portion to the belt portions by means of fastening means preferably arranged on the front portion.

Therefore there is a need for absorbent article provided with a belt, wherein the belt adapts itself to the user using the diaper and also feels comfortable to wear.

SUMMARY OF THE INVENTION

The object of the present invention is to provide a belted diaper or incontinence guard being comfortable to wear and which fits persons having different sizes. This object is being solved in that the belt portions are attached to the rear portion alternatively the front portion of the article via firsts elastic side panels being arranged on the article and that the front alternatively the rear portion of the article exhibits second elastic side panels to which fastening means are attached. These elastic side panels allow a flexibility of the position of the belt around the waist and distribute the forces evenly over the belt which gives an increased comfort.

SHORT DESCRIPTION OF DRAWINGS

The invention will in the following be closer described with reference to an embodiment shown in the accompanying drawing.

FIG. 1 schematically shows a view from the side of a diaper or incontinence guard according to the invention intended to be faced against the wearer during usage.

DESCRIPTION OF AN EMBODIMENT

The drawing shows an embodiment of a diaper or incontinence guard 1 comprising a liquid impermeable backsheet 2, a liquid permeable,topsheet 3 and an absorbent body 4 enclosed therebetween. The liquid permeable topsheet 3 can consist of a nonwoven material, e.g., a spunbond material of continuous filaments, a meltblow material, a bonded carded fibrous web or a perforated plastic film. The liquid impermeable backsheet 2 may consist of a plastic film, a non-woven material coated with a liquid impervious material or a hydro-phobic nonwoven material, which resists liquid penetration. The liquid impermeable backsheet 2 may also be a vapour permeable material.

The backsheet 2 and the topsheet 3 material have a somewhat greater extension in the plane than the absorbent body 4 and extend outside the edges thereof The layers 2 and 3 are connected to each other within the projecting portions thereof, eg., using gluing or welding by heat or ultrasonic, The absorbent body 4 can be of any conventional kind. Examples of commonly occurring absorbent materials are cellulose fluff pulp, tissue layers, highly absorbent polymers (so called superabsorbents), absorbent foam materials, absorbent nonwovens or the like, It is common to combine cellulose fluff pulp with superabsorbents in an absorbent body. It is also common to have absorbent bodies comprising layers of different material with different properties with respect to liquid acquisition capacity, liquid distribution capacity and storage capacity. It is well known to the person skilled in the art and does therefore not have to be described in detail. The thin absorbent bodies, which are common in for example baby diapers and incontinence guards, often comprise a compressed mixed or layered structure of cellulose fluff pulp and superabsorbent.

The diaper/incontinence guard is intended to enclose the lower part of the wearer's trunk like a pair of absorbent pants. It comprises a font portion 5 intended during use to be worn on the front part of the user's body, a rear portion 6 intended during use to be worn on the rear part of the user's body, and a crotch portion 7 located between the front and rear portions and which is intended to be worn in the crotch par of the user between the legs. The front portion 5 exhibits a pair of tape tabs 8 or another kind of fastening means such as hook and loop fasteners.

A pair of belt portions 9, 10 are with one end attached, e.g. glued or ultrasonically welded, to the rear portion 6 of the diaper. The belt portions 9, 10 are with their opposite ends intended to be fastened together by means of first fastening means 11, e.g. a hook-and-loop type fastener or tape tabs, intended to be attached against the outsides of the opposite belt portion. The second fastening means 8 of the front portion 5, such as for instance hook and loop fasteners or tape tabs, which are intended to be attached against the outsides of the belt portions 9, 10 in order to fasten together the diaper/incontinence guard to the desired pantlike shape.

According to an alternative embodiment the belt portions 9, 10 are attached to the front portion 5 of the diaper and thus are intended to be fastened 4 together on the back of the wearer The fastening means 8 are then arranged on the rear portion 6 of the diaper.

The width of the belt portions 9, 10 should be between 3–20 cm, preferably between 7–15 cm. The belt portions 9, 10 comprise according to an embodiment a laminate, wherein a carrier material forms the outside of the belt and a soft nonwoven forms the inside of the belt, intended to be in direct contact with the skin of the user. A suitable nonwoven material can be a spunbond material of e.g., polypropylene or polyethylene fibres. Conjugate fibres may also be used. Another suitable nonwoven material can be a carded thermobonded material of e.g., polypropylene, polyester or conjugate fibres. A plastic film or another suitable material e.g., nonwoven, may be used as crier material. The carrier material should be adapted to function as a reception surface for both the fastening means 8 and 11, wherein in the case where these are tape tabs, a plastic film is suitable. In the case wherein other kinds of fastenings measure is used instead of tape tabs, e.g., a hook and loop type fastener, another kind of carrier material is used, in particular a nonwoven material, which can act as a reception surface for the fastening means in question. Separate reception surfaces for fastening mean could also be arranged on the outsides of the belt.

The rear portion 6 is provided with first elastic panels 12, to which the belt portions 9, 10 are arranged. In another embodiment the front portion 5 is likewise provided with second elastic panels 13, to which fastening means 8 are arranged. The elastic side panels 12, 13 are elastic in both x-direction (essentially along the longitudinal direction of the belt) and in y-direction (essentially across the longitudinal direction of the belt). This leads to that the belt may be directed in different directions, The forces being put on the belt during the application of the article, is taken up by the elastic panels 12, 13, whereby the belt better follows the shape of the body. The elastic panels 12, 13 are a part of the rear portion 6 or the front portion 5, respectively and thereby substitutes a part of the so-called shell, comprised of the backsheet 2 and the topsheet 3.

According to an alternative embodiment, wherein the belt portions 9, 10 are attached to the front portion 5, said first elastic panels 12 will of course be arranged on the front portion 5 of the diaper. Analogously, said second elastic side panels 13 will be arranged next to the fastening means 8 arranged on the rear portion 6 of the diaper.

The material used for the elastic side panels 12, 13 can be a combination of an elastomeric polyurethane/elastomeric spunboud material, an elastic nonwoven material, an elastic laminate or an elastic film. It is important that the elastic material has elastic properties in both x-direction and y-direction, to achieve the desired fit. The side panels 12, 13 do not need to be of the same material, but may consist of two different materials having different properties. For example, the materials may mutually exhibit different properties regarding stretchability in x-direction and y-direction, respectively.

The invention is of course not limited to the above-described embodiment but can be modified within the scope of the claims.

What is claimed is:

1. An absorbent article comprising:
   a liquid permeable topsheet, a liquid impermeable backsheet, and an absorbent body enclosed therebetween;
   a front portion, a rear portion and a crotch portion therebetween;
   a pair of inelastic belt portions attached to the rear portion and which are fastenable together around a waist of a wearer; and
   a pair of first elastic side panels solely connecting each of said pair of inelastic belt portions to said rear portion,
   wherein one of said pair of belt portions has a first fastener arrangement connectable to another one of said pair of belt portions, and
   wherein said front portion has a second fastener arrangement connectable to said pair of belt portions, such that the article will assume a pantlike shape, so that said pair of belt portions form a part of a waist portion of the article.

2. The absorbent article according to claim 1, wherein the front portion further comprises second elastic side panels, said second fastener arrangement being attached thereto.

3. An absorbent article comprising:
   a liquid permeable topsheet, a liquid impermeable backsheet, and an absorbent body enclosed therebetween;
   a front portion, a rear portion and a crotch portion therebetween;
   a pair of inelastic belt portions attached to the front portion and which are fastenable together around a waist of a wearer; and
   a pair of first elastic side panels solely connecting each of said pair of inelastic belt portions to said front portion,
   wherein one of said pair of belt portions has a first fastener arrangement connectable to another one of said pair of belt portions, and
   wherein said rear portion has a second fastener arrangement connectable to said pair of belt portions, such that the article will assume a pantlike shape, so that said pair of belt portions form a part of a waist portion of the article.

4. The absorbent article according to claim 3, wherein the rear portion further comprises second elastic side panels, said second fastener arrangement being attached thereto.

5. An absorbent article comprising:
- a liquid permeable topsheet, a liquid impermeable backsheet, and an absorbent body enclosed therebetween;
- a front portion having a first end edge, a rear portion having a second end edge and a crotch portion therebetween;
- a pair of inelastic belt portions attached to the rear portion and which are fastenable together around a waist of a wearer; and
- a pair of first elastic side panels connecting each of said pair of inelastic belt portions to said rear portion at said second end edge, wherein one of said pair of belt portions has a first fastener arrangement connectable to another one of said pair of belt portions, and wherein said front portion has a second fastener arrangement connectable to said pair of belt portions, such that the article will assume a pantlike shape, so that said pair of belt portions form a part of a waist portion of the article.

6. The absorbent article according to claim 5, wherein the front portion has second elastic side panels connected at said first end edge, said second fastener arrangement being attached to said second elastic side panels.

* * * * *